United States Patent [19]

Guillet et al.

[11] Patent Number: 5,374,339
[45] Date of Patent: Dec. 20, 1994

[54] PRODUCTION OF HYDROGEN PEROXIDE

[76] Inventors: James E. Guillet, 31 Sagebrush Lane, Don Mills, Ontario, Canada; Gad Friedman, 3 Hazait Street, Rehovot, 76349, Israel

[21] Appl. No.: 136,020

[22] Filed: Oct. 14, 1993

[51] Int. Cl.$^5$ .................... C01B 15/024; C01B 15/026
[52] U.S. Cl. .................... 204/157.5; 423/588
[58] Field of Search .................... 204/157.5, 157.52; 423/588

[56] References Cited

U.S. PATENT DOCUMENTS

| | | | |
|---|---|---|---|
| 4,349,526 | 9/1982 | Goor et al. | 423/588 |
| 4,576,687 | 3/1986 | Hertl et al. | 204/157.5 |
| 4,946,566 | 8/1990 | Stevens et al. | 204/157.5 |

OTHER PUBLICATIONS

Tickle and F. Wilkinson, *Trans. Farad. Soc.,* 61, pp. 1981–1990 (Apr., 1965).

*Primary Examiner*—Wayne Langel
*Attorney, Agent, or Firm*—Ridout & Maybee

[57] ABSTRACT

Hydrogen peroxide is produced by a process which uses solid, insoluble, supported anthraquinone as catalyst. The catalyst is reduced to supported anthrahydroquinone using a hydrogen-donating organic substrate such as an alcohol, followed by reaction with oxygen, suitably photochemical reaction, to regenerate anthraquinone and to form hydrogen peroxide, which can be solvent extracted from the solid catalyst.

12 Claims, No Drawings

PRODUCTION OF HYDROGEN PEROXIDE

FIELD OF THE INVENTION

This invention relates to anthraquinone catalyzed chemical processes and especially to methods for manufacture of hydrogen peroxide, using anthraquinone as a catalyst.

BACKGROUND OF THE INVENTION

The photochemical reaction between alcohols and oxygen sensitized by quinone catalysts has been studied for a number of years. For example, Tickle and Wilkinson[1] studied the photooxidation of isopropanol (2-propanol) using anthraquinone (AQ) as a catalyst. The overall stoichiometry of the reaction is

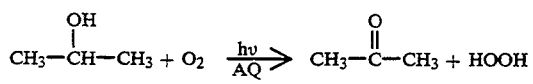

The mechanism is proposed to involve the photoreduction of AQ via its triplet State to form anthrahydroquinone which is converted back to the starting catalyst AQ with air or oxygen with the concurrent formation of HOOH.

An analogous reaction involving the catalytic reduction of an alkyl anthraquinone by hydrogen is the basis of a current industrial synthesis of hydrogen peroxide (HOOH) via the reaction sequence

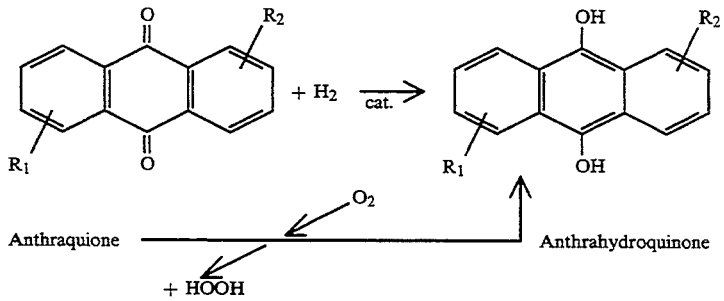

where $R_1$ and $R_2$ can be hydrogen or $C_1$-$C_{20}$ alkyl groups

Hydrogen peroxide is an important industrial chemical. It is widely used as a bleach, e.g. in the pulp and paper industry. It is also used extensively in the mining industry, e.g, for removing cyanide residues from gold mining operations. It is basically an environmentally acceptable chemical, unlike many competitive industrial bleaching compounds. Hydrogen peroxide is however a difficult material to transport safely. The locations where it is to be used industrially, e.g. mining sites and pulp mills, are often far removed from other chemical manufacturing and processing facilities. The production of the required hydrogen peroxide on site is accordingly desirable.

AQ derivatives are widely used in industrial process for the production of hydrogen peroxide. The AQ derivative is hydrogenated to anthrahydroquinone (AHQ), which is subsequently oxygenated to AQ and hydrogen peroxide. Separation of the AQ from the product is complicated and costly. Liquid-liquid extraction, to take out the hydrogen peroxide product as an aqueous solution, is necessary. This is costly, and involves large volumes of recycle. Quantitative separation is not achieved. Only dilute solutions of hydrogen peroxide are obtained, unless subsequent distillation is undertaken.

It is an object of the present invention to provide novel methods of conducting anthraquinone-catalyzed chemical processes, which overcome or at least reduce one or more of the aforementioned disadvantages.

It is a further object to provide a novel process for production of hydrogen peroxide.

SUMMARY OF THE INVENTION

This invention provides methods by which an anthraquinone (AQ) moiety is immobilized on an inert, non-soluble carrier. The immobilized AQ maintains its chemical reactivity. It can be utilized for most of the chemical procedures in which AQ is used as a catalyst; it can be recycled, and it is easily separated from other reactants.

Examples of processes where this novel, immobilized AQ can be used include: photochemical oxidation of alcohols, photochemical production of hydrogen peroxide, formation of hydrogen peroxide by chemical reduction of the AQ followed by air oxidation, and other radical reactions initiated by (photochemical) hydrogen abstraction.

The immobilized AQ is able to undergo a multitude of reaction cycles retaining its activity and efficiency for a large number of turnovers; thus it can be regarded as a true (photo) catalyst.

The process of the present invention very significantly reduces the problems of separation and recovery of the AQ catalyst and product, while maintaining the activity of the AQ moiety.

The process of the present invention offers several advantages over the current methods involving the AQ-AHQ cycle.

(a) The immobilization of AQ onto the solid supports prevents consumption or loss of this molecule during the process. It is easily retrieved when the reaction is stopped, and avoids contamination of the working solutions and effluents.

(b) AQ immobilized on the totally inert inorganic supports has a special advantage over similar products where organic polymers are utilized as carriers. This is manifested, for example, in the photochemical process. AQ which was chemically attached to an organic polymer exhibited spectroscopic evidence for the reversible photochemical reduction and air oxidation as observed in organic AQ solution, However, the reactive intermediates attack the supporting polymer, consuming its available hydrogen atoms.[2] This is not the case with inert inorganic supports.

(c) The ability of the immobilized AQ to function in aqueous and in polar and non polar organic solutions is of particular interest and significance. The common industrial process for hydrogen peroxide manufacture, "The AQ Process"[3], is complicated by changes in the reagent's solubility. AQ is soluble in organic non-polar solvents. The AQ is hydrogenated to form AHQ which is soluble in organic polar solvents. Oxygen is blown in, and the AHQ is transformed back to AQ while releasing hydrogen peroxide. The hydrogen peroxide is collected by extraction with water. Special efforts are made to overcome the solubility problems and to minimize AQ losses. The immobilized AQ used in the process of the present invention can be integrated into the current process of HOOH manufacture. It bypasses these complications. It is active in aqueous as well as organic solutions. No losses of immobilized AQ to the solvents have been observed.

This invention has the potential for producing hydrogen peroxide photochemically, using natural hydroxy compounds (alcohols, carbohydrates, polycarbohydrates) as hydrogen donors, thus enabling the preparation of this important chemical where light and the above-mentioned raw materials are abundant. Alternatively, these alcohols can be utilized to reduce the carbonyl functions of AQ in a catalyzed transfer hydrogenation reaction.[4]

DESCRIPTION OF THE PREFERRED EMBODIMENTS

The invention includes methods to activate silica or glass in the form of beads, loose powder, fibres, tubes, or plates by using silane coupling molecules, e.g., amino propyl trimethoxy silane (APTS), and a method to bind AQ thereto. Anthraquinone (in the form of AQ carboxylic acid chloride) is covalently bound to the free amino functions which have thus been attached to the silica/glass. The amount of AQ immobilized by this method relates to the accessible surface area of the silica/glass. High densities of amino groups can be obtained by proper choice of technique.[5]

Alternatively, an AQ (e.g., in the form of 2-isopropenyl or AQCH=CHCOOH) moiety can be copolymerized with, e.g., acrylic acid or any of its derivatives. This polymer is attached to the amine activated silica via its functional group—the carboxylic group—with the aid of coupling agents such as dicyclohexyl carbodiimide (DCC). This approach enables heavier loading of AQ on silica. Moreover, changing the co-monomer can provide AQ catalysts with varying affinity and effectivity towards solvents and substrates.

In a similar process, the silica is functionalized with β-(trimethoxysilicyl)propyl methacrylate followed by polymerization with a mixture of vinyl AQ and co-monomer. Anthraquinone-2-carboxylic acid chloride (AQCOCl) can be attached to cellulosefibres by a route which resembles its binding to silica. Other methods which are commonly used by the dyeing industry, can be utilized to affix AQ to cellulose fibres.

In addition to anthraquinone-2-carboxylic acid derivatives, other suitable quinoid systems can be utilized to perform similar reactions. Among those are anthraquinone-2-sulfonic acid (AQ-2-SO$_3$H), 2,6- or 1,5-disulfonic acid (AQ-2,6-diSO$_3$H; AQ-1,5-diSO$_3$H) and their derivatives and other members of the anthraquinone group substituted by electron-withdrawing moieties such as chlorine atoms, and also benzoquinone and benzanthrone.[6,7]

Several organic alcohols have displayed this hydrogen donor ability: primary alcohols (ethanol and n-butanol), secondary alcohols (isopropanol and sec-butanol), polyols (glycerol and the sugars sucrose and xylose).

In one preferred method of application of our invention, the immobilized AQ is suspended in the (liquid) substrate. Air is blown through this suspension in order to stir it and to supply oxygen. Irradiation at 360 nm or shorter wave length induces photoreduction of the AQ to AHQ. In the presence of air or oxygen, this is subsequently oxygenated to yield hydrogen peroxide and the hydrogen-donating co-reagent is concurrently oxidized. For example, irradiation of immobilized AQ in isopropanol leads to the formation of hydrogen peroxide and acetone. The reaction can take place in a suspension of the pure co-reagent or in its aqueous solution.

This process can also be performed in two distinct and separate stages. For example, the photochemical hydrogen abstraction can be performed (in the absence of oxygen) in a solution of hydrogen donor, e.g, isopropanol, which can be then removed from the reacting beads. Hydrogen peroxide can be harvested from the solid catalyst in a second medium, e.g., water after exposure to oxygen. This route of alternating reaction media has the advantage of collecting the hydrogen peroxide in a pre-selected medium, free from starting materials.

One can also obtain high yields of hydrogen peroxide by continuous irradiation in the presence of air. This process is believed to take place via the excited triplet state of the anthraquinone moiety and these excited states are known to be quenched by oxygen. It appears that the rate of photoreduction on these highly active catalysts can compete effectively with quenching by oxygen.

In the non-photochemical route, the immobilized AQ is converted to AHQ with the aid of soluble reducing agents such as sodium borohydride or sodium dithionite or hydrogenation using homogeneous catalysts which are known to reduce carbonyl functions such as ruthenium triphenylphosphine complexes.[8]

The basic reactions and structures can be represented as follows:

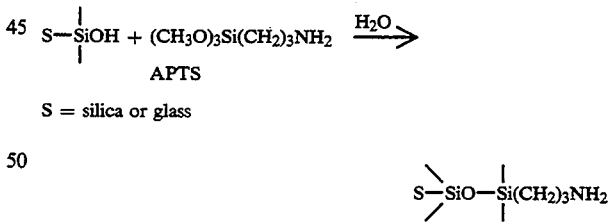

S = silica or glass

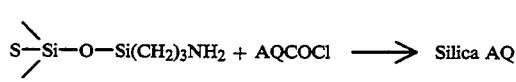

The chemical structures are summarized below.

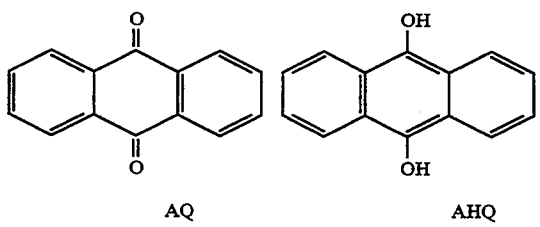

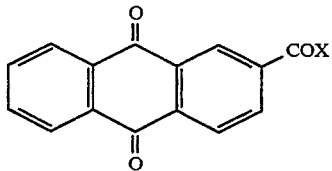

X = OH — Anthraquinone-2-carboxylic acid AQCOOH
Y = Cl — Anthraquinone-2-carboxylic acid chloride AQCOCl

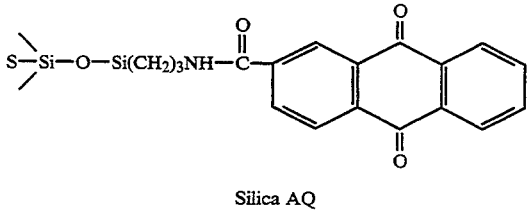

Silica AQ

SPECIFIC DESCRIPTION OF THE MOST PREFERRED EMBODIMENTS

Example 1

Activation of Silica-Gel Beads

Aminopropyl trimethoxysilane (APTS, 2 g) was added to 100 ml of water. Acetic acid was added dropwise to pH 4. After brief stirring, 20 g of silica gel beads (60–120 mesh, BDH) were added. After one hour the aqueous solution was decanted. The silica was washed with water and ethanol, and air dried overnight. These activated beads were further reacted with AQ derivatives (see examples below) and have over 0.11 mmol free amine/g as evidenced by the amount of binding.

Higher densities of amino groups can be obtained by refluxing silica with APTS in toluene.[5]

Example 2

Activation of Glass Fibres

Pyrex glass fibres (5 g) were treated with sodium hydroxide (20% solution) for ca. 30 min. at room temperature. The base was rinsed and the fibres washed thoroughly with water, dilute hydrochloric acid, and ethanol, and then air dried. The fibres were than treated with an aqueous APTS mixture as described in Example 1.

Example 3

Binding of AQCOCl to Fumed Silica

Fumed silica (Cab-o-Sil M5, Cabot Corp., 5 g, activated with APTS, as described in Example 1 and dry tetrahydrofuran (THF, 50 mL) was stirred in a flask. AQCOCl (220 mg) in 10 mL of THF was added dropwise. After 30 min., ca. 0.5 mL of pyridine was added and the mixture stirred for an additional 1 hour. The modified silica was filtered, thoroughly washed with ethanol, and then dried. The washings contained about 50 mg of AQCOOEt and AQCOOH (as determined by UV adsorption at 324 nm) indicating that ca. 0.126 mmol/g of AQ was immobilized on the surface of the silica.

Example 4

Binding of AQCOCl to Silica Gel

Silica gel 60 (5 g, 230–400 mesh, EM Science, APTS activated as in 1) was reacted with 165 mg AQCOCl as in Example 3. Analysis of the washing shows that 159 mg (0.11 mmol/g) AQ were bound to the silica beads.

Example 5

Binding of AQCOCl to Pyrex Glass Fibres

Pyrex glass fibres activated with APTS (5 g) were reacted with AQCOCl (55 mg) by procedure of Example 3. Analysis of the washings determined that 35 mg (0.026 mmol/g) of AQ was bound.

Example 6

BiO glass 1500 (porous glass for chromatography, Bio-Rad) was reacted with AQCOCl by the procedure of Example 3. Bound AQ 0.045 mmol/g.

Example 7

Binding of AQCOCl to Cellulose

Cellulose pulp (2 g) was stirred in water for 24 hours. The water was removed and the pulp soaked in dry methanol. Methanol was drained off and a new portion was added. This was repeated four times, followed by similar cycles using dry THF. Finally, 10 mg of AQCOCl was added. After 5 hours a few drops of pyridine was added and the mixture was stirred overnight. Analysis of the washings indicates that 0.01 mmol of AQ was bound to the pulp.

Example 8

Binding of AQCOOH to Silica Gel

To 5 g of aminopropyl-functionalized silica gel (Aldrich, ~9% functionalized) in 75 mL dry THF, were added 1.26 g AQ-COOH and 1.2 g DCC. The mixture was stirred overnight and then filtered, washed with acetone, methanol, water and acetone, and then dried. Analysis of the washings showed that 1.18 g (0.94 mmol/g) AQ were bound to the silica.

Example 9

Binding of AQ-2-SO$_3$H to Silica

AQ-2-SO$_3$Na (Aldrich) was converted to AQ-2-CO$_2$Cl with the aid of thionyl chloride.[9] The chloride (0.3 g, 1 mmol) was reacted with 4 g of aminopropyl-functionalized silica in THF. After 1 h, pyridine (0.5 mL) was added. The mixture was stirred for 12 h, filtered, washed with EtOH, and then dried. Examination of the washings showed that the binding was nearly complete, i.e., 0.25 mmol/g).

Example 10

Binding of AQ-2,6-diSO$_3$H to Silica

AQ-2,6-diSO$_3$Na was converted to AQ-2,6-diSO$_2$Cl.[9] To a stirred suspension of aminopropyl-functionalized silica (3 g) in THF, was added 0.33 g (0.15 mmol) of the dichloride. After 1 h, pyridine (0.5 mL) was added and the mixture was stirred for an additional 12 h. Silica particles were filtered, washed with acetone, then with dilute Na$_2$CO$_3$, acetone and dried. Analysis of the washings showed that the whole amount was practically bound, i.e, loading of 0.25 mmol/g.

Example 11

Irradiation of Silica-AQ with Alcohols and Water Alcohol Mixtures

The irradiation experiments were performed in a Pyrex tub-shaped reactor equipped with a fitted glass at the bottom, an inlet side-arm and a tap. Air or nitrogen was supplied through the side-arm and the fritt, stirring the reaction mixture and forming either an oxidative or inert atmosphere.

Alternatively, these gases were supplied via the top forcing the liquid out while maintaining the desired atmosphere. A condenser at the top prevented loss of volatiles. This reactor was placed in a Rayonette irradiation well apparatus 16 360-nm lamps. Air was bubbled via the fitted glass and coolant was circulated in the condenser.

Irradiation experiments were carried out for 1-2 h. The amount of $H_2O_2$ produced was determined by an iodometric method for the organic reaction mixtures. The aqueous solutions were analyzed via titanate formation.[10] Several experimental examples are summarized in Table 1.

TABLE 1
HYDROGEN PEROXIDE FORMATION BY IRRADIATION OF IMMOBILIZED AQ WITH ALCOHOLIC HYDROGEN DONORS

| | Catalyst (mg) | Substrate | Irradiation (h) | $H_2O_2$ mol (mmol) | $H_2O_2$/ mol AQ |
|---|---|---|---|---|---|
| (a) | 120[a] | iPrOH | 1 | 0.32 | 33 |
| (b) | 100[a] | iPrOH (40% in $H_2O$) | 1 | 0.14 | 17 |
| (c) | 100[a] | iPrOH (20% in $H_2O$) | 1 | 0.1 | 12 |
| (d) | 120[a] | iPrOH | 2 | 0.47 | 60 |
| (e) | 100[a] | nBuOH | 1 | 0.3 | 37 |
| (f) | 100[a] | 2-BuOH | 1 | 0.19 | 24 |
| (g) | 100[a] | Ethanol | 1 | 0.38 | 47 |
| (h) | 100[a] | nBuOH (20% in $H_2O$) | 1 | 0.05 | 6 |
| (i) | 100[a] | 2-BuOH (20% in $H_2O$) | 1 | 0.01 | 1 |
| (j) | 100[a] | Ethanol (20% in $H_2O$) | 1 | 0.02 | 2.5 |
| (k) | 100[a] | Glycerin (20% in $H_2O$) | 1 | 0.03 | 3.6 |
| (l) | 100[a] | Sucrose (20% in $H_2O$) | 1 | 0.02 | 2.4 |
| (m) | 655[a] | iPrOH | 1 | 0.02 | 40 |
| (n) | 655[b] | $H_2O$ | 1 | >0.004 | |
| (o) | 100[d] | xylose (5% in $H_2O$) | 1 | 0.0053 | 2 |
| (p) | 100[c] | sucrose (5% in $H_2O$) | 1 | 0.253 | 11 |
| (q) | 100[c] | iPrOH (40% in $H_2O$) | 1 | 2.464 | 110 |
| (r) | 500[c] | xylose (5% in $H_2O$) | 1 | 0.3 | 2.4 |

[a]Cab-o-sil M5: AQ content, 0.08 mmol/g, as made in Example 3.
[b]Cellulose pulp: AQ content, 0.005 mmol/g, as made in Example 2.
[c]Aminopropyl silica (Aldrich) AQ (as $AQSO_2NH$—) content 0.25 mmol/g as made in Example 9.
[d]Aminopropyl silica (Aldrich) AQ content 0.94 mmol/g as made in Example 8.

Example 12

Alternating Cycles of Photoreduction and Oxygenation

The reaction vessel was charged with 200 mg of silica AQ (0.02 mmol/g), 10 mL of iPrOH, and a constant stream of nitrogen was passed through the fritt. The reactor was irradiated for 5 min. Alcohol was forced out from the reactor with the aid of nitrogen. Water (5 mL) was introduced and air was bubbled for 3 min. The aqueous solution was filtered and kept. The reaction vessel was flushed with nitrogen and the iPrOH solution was re-introduced and irradiated. After five alternating cycles the aqueous solution contained 0.014 mmol of hydrogen peroxide, i.e, production of 3.5 mol $H_2O_2$/mol AQ.

Example 13

Preparation of Hydrogen Peroxide Via Sodium Borohydride Reduction

Silica AQ (2 g, 60-120 ~0.06 mmll/g AQ) as prepared in Example 5 was suspended in ethanol (in the reactor described above) with the aid of a fine stream of nitrogen. Sodium borohydride (0.145 g) was added and the mixture reacted for 30 min. The solvent was filtered off and washed with ethanol under a nitrogen atmosphere. Finally, ethanol was added to the particles and air blown for ~5 min. The solution was collected and the hydrogen peroxide determined to be 0.34 mg. Similar results were obtained using sodium dithionite as the reducing agent.

Example 14

Photooxidation of Glycerine

Aqueous glycerine (10 mL, 20% glycerine) was irradiated with 120 mg silica AQ (0.08 mmll/g) for 5 h with air blowing through the mixture. GC analysis determined formation of dihydroxy acetone (0.85 mmol, 17 mol/mol AQ/h).

Example 15

Irradiation of Toluene

Toluene (10 mL) and silica AQ (120 mg, 0.08 mmol AQ/g) were irradiated as above (5h). GC analysis demonstrated the formation of benzaldehyde (44 mg, 0.36 mmol, 4.5 mol/mol AQ) as well as benzoic acid. Analysis of the toluene by the iodometric method showed that 0.4 mmol (5 mol/mol AQ) of peroxide was formed.

Example 16

Preparation of Acrylic Acid 2-Isopropenyl Anthraquinone Copolymer 2-isopropenyl AQ (0.3 g), 1.2 g acrylic acid (Aldrich, containing inhibitors (200 ppm MEHQ) and 40 mg AIBN were placed in a heavy-walled glass tube. Oxygen was removed by three freeze/thaw cycles. The tube was sealed and heated to 80° C. for 1 h. The polymer thus obtained was dissolved in dioxane. TLC (20% AcOEt in hexane) shows disappearance of free isopropenyl AQ.

Example 17

Binding of Poly(acrylic) 2-Isopropenyl AQ to Silica APTS

Silica 60 APTS (2 g) was added to 20 mL dry dioxane solution containing 0.5 g of polymer. Dicyclohexyl carbodiimide (DCC) 85 mg was added and the mixture was stirred overnight, then filtered and washed with dioxane ethanol, acetone and dried. Irradiation of 20% aqueous isopropanol for 1 h as in Example 9 yielded 0.08 mmol $H_2O_2$ in the effluent from the catalyst.

Example 18

Solar Irradiation

The procedure of Example 11a was repeated except that the reactor was placed in bright summer sunlight for 5 h. The yield of hydrogen peroxide was 0.28 mmol.

Example 19

Preparation of Methyl Methacrylate-acrylic Acid 2-Isopropenyl Anthraquinone Terpolymer 2-isopropenyl AQ (0.3 g), 0.5 g acrylic acid and 0.7 g methyl acrylate (Aldrich) containing inhibitor (200 ppm methyl hydroquinone, MeHQ) and 40 mg 2,2'-azobis-isobutyronitrile (AIBN) were placed in a heavy-walled glass tube. Oxygen was removed by three freeze/thaw cycles. The tube was sealed and heated to 80° C. for 1 h. The polymer thus obtained was dissolved in dioxane. TLC (20% AcOEt in hexane) shows disappearance of free isopropenyl AQ.

A 1% solution of the polymer in dioxane was sprayed on filter paper (Whatman #1) and dried. The filter paper was cut into small square pieces (ca. 5×5 mm). The impregnated paper pieces were suspended in the 20% iPrOH water mixture and irradiated as in Example 11 for 1 h. Hydrogen peroxide (0.07 mmol) was produced.

REFERENCES

1. Tickle and F. Wilkinson, *Trans. Farad. Soc.*, 61, 1981 (1965).

2. V. P. Foyle, Y. Takahashi and J. E. Guillet, *J. Polym. Sci., Polym. Chem. Ed.*, 30, 257 (1992).

3. W. Kunkel and O. Weiberg, in *Ulman's Encyclopedia of Industrial Chemistry*, 5th Ed., VCH Verlagsgesellschaft, Weinheim, 1989, vol. 13a, p. 443.

4. E. G. R. L. Chowdhury and E. Backvoll, *J. Chem. Soc., Chem. Commun.* 1063 (1991).

5. E. Angeletti, C. Canepa, G. Martinetti and P. Venturello, *J. Chem. Soc., Perkin Trans. I*, 105 (1989).

6. K. Lang, D. M. Wagnerova, P. Stopka and W. Damerau, *J. Photochem. Photobiol, A, Chem.*, 67, 1987 (1992).

7. C. F. Wells, *Trans. Faraday Soc.*, 57, 1703 (1961).

8 E.g., W. Strohmier and L. Weigelt, *J. Organomet. Chem.*, 171, 121 (1979); R. A. Sanchez-Delgado and O. L. De Ochoa, ibid., 202, 427 (1980).

9. A. M. Aquino, C. J. Abelt, K. L. Berger, C. M. Darraguh, S. E. Kelly and M. V. Cossette, *J. Amer. Chem. Soc.*, 112, 5819 (1990).

10. *Colorimetric Determination of Non-metals*, D. F. Boltz and J. Howell, eds., Wiley, 19, p. 301.

We claim:

1. A process for producing hydrogen peroxide, which comprises preparing supported anthrahydroquinone moieties bound to an insoluble, solid, inert support by photochemical reaction of similarity supported anthraquinone moieties with a hydrogen-donating organic substrate, reacting oxygen with said supported anthrahydroquinone moieties, so as to oxidize them to supported anthraquinone moieties, and recovering the hydrogen peroxide so formed as a solution thereof.

2. The process of claim 1, wherein the hydrogen-donating organic substrate is an organic alcohol.

3. The process of claim 2, wherein the organic alcohol is a primary alcohol, a secondary alcohol or a polyol.

4. The process of claim 1, wherein the solid inert support is silica, glass, polyethylene or cellulose.

5. The process of claim 4, wherein the support is silica or glass.

6. The process of claim 2, wherein the supported anthraquinone moieties are suspended in liquid organic substrate, air is blown into the suspension under photochemical irradiation of wavelength 360 nm or less, and hydrogen peroxide is solvent extracted from the reaction mixture.

7. The process of claim 6, wherein the liquid organic substrate is isopropanol, and acetone is additionally recovered from the reaction mixture.

8. A two-stage process for the production of hydrogen peroxide, which comprises:

in a first stage, photochemically reacting a hydrogen-donating organic substrate with supported anthraquinone moieties bound to an insoluble, solid, inert support so as to reduce the supported anthraquinone moieties to supported anthrahydroquinone moieties;

and, in a second stage, reacting the supported anthrahydroquinone moieties with oxygen to produce hydrogen peroxide and to re-form supported anthraquinone moieties ready for further reaction in a repeated first stage.

9. The process of claim 8 wherein said hydrogen-donating organic substrate is an alcohol.

10. The process of claim 9 wherein the alcohol is a primary alcohol, a secondary alcohol or a polyol.

11. The process of claim 8 wherein the solid, inert support is silica, glass, polyethylene or cellulose.

12. The process of claim 10 wherein the solid, inert support is silica or glass.

* * * * *